United States Patent [19]
Kozak

[11] Patent Number: 5,985,854
[45] Date of Patent: Nov. 16, 1999

[54] PRODRUGS WITH ENHANCED PENETRATION INTO CELLS

[75] Inventor: Alexander Kozak, Rehovat, Israel

[73] Assignee: D-Pharm, Ltd., Rehovat, Israel

[21] Appl. No.: 08/481,243

[22] PCT Filed: Mar. 30, 1994

[86] PCT No.: PCT/GB94/00669

§ 371 Date: Aug. 21, 1995

§ 102(e) Date: Aug. 21, 1995

[87] PCT Pub. No.: WO94/22483

PCT Pub. Date: Oct. 13, 1994

[30] Foreign Application Priority Data

Mar. 31, 1993 [IL] Israel ......................................... 105244

[51] Int. Cl.$^6$ ........................ A61K 31/66; A61K 31/685; A61K 31/215; A61K 31/19
[52] U.S. Cl. ................ 514/75; 514/77; 514/78; 514/529; 514/557
[58] Field of Search .............. 436/71; 562/566; 514/75, 77, 78, 529, 551

[56] References Cited

U.S. PATENT DOCUMENTS

| | | |
|---|---|---|
| 5,149,794 | 9/1992 | Yatvin et al. . |
| 5,227,514 | 7/1993 | Meul et al. . |

FOREIGN PATENT DOCUMENTS

| | | |
|---|---|---|
| 0275005 | 7/1988 | European Pat. Off. . |
| 0325160 | 7/1989 | European Pat. Off. . |
| 3133987 | 6/1991 | Japan . |
| 679856 | 4/1992 | Switzerland . |
| 8905358 | 6/1989 | WIPO . |
| 9000555 | 1/1990 | WIPO . |
| 9010448 | 9/1990 | WIPO . |
| 9116920 | 11/1991 | WIPO . |
| 9300910 | 1/1993 | WIPO . |
| 9408573 | 4/1994 | WIPO . |

OTHER PUBLICATIONS

NTIS Technical Notes, No. 9, 19847, "Prodrugs based on phpospholipid–nucleoside conjugates" Springfield, VA, p. 630.

Stuttgart, DE, Geb. 1992: European J. of Pharmaceutics and Biopharmaceutics, 38(1):1–6. O. Vaizoglu et al., Jul. 26, 1989, EP–A–0325 160 (Hoechst A.G.).

Hostetler et al., Jun. 1991, "Phosphatidylaazothymidine. Mechanism of antiretroviral action in cem cells." J. Biol. Chem. 266(18):11714–11715.

Gusovsky et al., Feb. 1990, "Mechanism of maitotoxin–stimulated phosphoinositide breakdown in HL–60 cells." J. Pharmacol. Ex. Ther. 252(2):469–470.

Govez–Cambronero et al., Apr. 1991, "Platelet–activating factor induces tyrosine phossssphorylation in human neutrophils." J. Biol. Chem. 266(10):6240–5.

Natarajan et al. "Activation of endothelial cell phospholipase D by hydrogen peroxide and fatty acid hydroperoxide." J. Biol. Chem 268(2):930–7.

(List continued on next page.)

*Primary Examiner*—Gollamudi S. Kishore
*Attorney, Agent, or Firm*—Davidson, Davidson & Kappel, LLC

[57] ABSTRACT

The invention relates to a pharmaceutically acceptable prodrug which is a covalent conjugate of a pharmacologically active compound and an intracellular transporting adjuvant, characterized by the presence of a covalent bond which is scission-sensitive to intracellular enzyme activity. The prodrug may be used in a technique for treating a condition or disease in a human related to supranormal intracellular enzyme (.e.g. phospholipase and/or esterase) activity, whereby on administering it to a human having such condition or disease, the bond is broken in response to such activity, and the pharmacologically active compound accumulates selectively within cells having such supranormal intracellular enzyme activity. Exemplary conjugates are esters of the carboxylic function in the formula, with e.g. heptanoyl-sn-3-glycerophosphoryl-choline or octanoyl-sn-3-glycerophosphoryl-choline.

17 Claims, 11 Drawing Sheets

OTHER PUBLICATIONS

Coorssen et al., "GTP.gamma.S and phorbol ester act synergistically to stimulate both calcium independent secretion and phospholipase D activity in permeabilized human platerits. Inhibition by BAPTA and analogs" FEBS LETT.316(2):170–4.

Duan et al., Feb. 1994, "Conversion to CA(2+)–independent form of Ca2+/calmodulin protein kinase II in rat pancreatic acini." Biochem. Biophys. Res. Commun. 199(1):368–373.

AXIS:
 X – FORWARD SCATTERING
 Y – INTRACELLULAR CALCIUM LEVEL (au)
   L – LOW CALCIUM LEVEL
   H – HIGH CALCIUM LEVEL
 Z – EVENTS $y = 15.626 LOG(x) + 13.658$ $r^2 = 0.965$

NORMAL FLOW

LOW-FLOW PERFUSION: AV-BLOCK

REPERFUSION VENTRICULAR FIBRILLATION

PRODRUGS WITH ENHANCED PENETRATION INTO CELLS

This application is 371 of PCT/GB94/00669 filed Mar. 30, 1996.

FIELD OF THE INVENTION

The present invention relates to a technique for treating a condition or disease in a human related to supranormal intracellular enzyme activity, and to a prodrug useful in such technique.

BACKGROUND OF THE INVENTION

Many major diseases in humans, including ischemia, stroke, epilepsy, asthma and allergy are believed to be related to the phenomenon of cell hyperexcitation, a term used herein to denote abnormally elevated levels of certain intracellular enzymes. For instance, as a result of supranormal intracellular phospholipases associated with these disease states, cell membranes are broken down. Current pharmacological strategies are therefore aimed at inhibiting this deleterious degradative activity.

It would be useful to be able to selectively target diseased cells characterized by enzyme hyperactivity, so as to introduce a pharmacologically active molecule in the form of a prodrug into a cell, whereby such hyperactivity would act on the prodrug, so that the pharmacologically active molecule accumulates in the diseased cells rather than in the healthy cells.

A non-limiting example of such a pharmacologically active molecule is a calcium chelating agent, which would have many advantages over drugs presently used for the treatment of calcium associated disorders.

Intracellular calcium is an important determinant for cell death, irrespective of the initial insult sustained by the cell. It may be involved in cell death in lymphocyte and killer cell mediated damage of target cells, in organ damage during transplantation, and in other types of tissue damage including ischemic insults. Calcium channel blockers or cell membrane permeable forms of calcium chelators have been suggested to protect against tissue injury or to decrease tissue damage. Thus, it will be apparent that the present invention has potential use (in the embodiment employing a calcium chelator) in relation to these circumstances.

It will also be self-evident that a similar concept can be applied to the treatment of conditions or diseases other than those related to the intracellular level of calcium ions. By way of example, if the active entity incorporated in the prodrug molecule is a protein kinase inhibitor, after administration of the prodrug the inhibitor would accumulate in a cell exhibiting abnormal proliferation, thus potentially providing an important tool for use in antitumor therapy.

The use of prodrugs to impart desired characteristics such as increased bioavailability or increased site-specificity on known drugs is a recognized concept in the state of the art of pharmaceutical development. The use of various lipids in the preparation of particular types of prodrugs is also known in the background art. In none of those instances are the prodrugs characterized in that they achieve preferential accumulation of the drug within the diseased cells of the organ, by activation with intracellular lipases. Rather, they provide for the drug to be transported to a specific site, or to be released within a specific organ. This appraoch is exemplified in the case of the phospholipid prodrugs of salicylates and non-steroidal anti-inflammatory drugs disclosed in WO 91/16920 which, taken orally, protect the gastric mucosa and release the active principle in the gut.

In other examples of phospholipid prodrugs, the formulation of the prodrugs into liposomes or other micellar structures is the feature that enables their preferential uptake, for instance by macrophages or by liver cells as in the case of the phospholipid conjugates of antiviral drugs disclosed in WO 90/00555 and WO 93/00910.

Generally, viral infection is not associated with supranormal phospholipase activity and antiviral phospholipid conjugates do not teach or suggest activation of the drug preferentially in the diseased cells, or in the infected cells as in the case of the phospholipid conjugates of antiviral nucleotides and anti-sense oligonucleotides, such as those disclosed in WO 90/00555, in WO 90/10448 and in NTIS Technical Notes, no. 9, page 630, Springfield, Va., US, 1984.

In other instances specific types of polar lipids are used to target the prodrugs to intracellular organelles as in the case of the antiviral and antineoplastic nucleosides disclosed in U.S. Pat. No. 5,149,794. Additional types of lipids have also been used in specific types of prodrugs such as EP A-325160 which discloses glycerin esters of ACE inhibitors, which form micelles absorbed from the incestine into the lymphatic system, thereby bypassing the liver and having increased access to the central nervous system, for use in the treatment of hypertension and cognitive dysfunction. The ACE inhibitors undergo enzymatic cleavage and exert their therapeutic effects extracellularly.

Other types of lipophilic carriers that facilitate intracellular transport are known in the art, as in CH A-679856 which discloses the use of salicyloyl-carnitine for the treatment of pain, and in WO 89/05358 which discloses modified oligonucleotide antisense drugs, transported into cells by attachment of apolar groups such as phenyl or naphthyl groups.

SUMMARY OF THE INVENTION

In accordance with one object of the invention, there are provided prodrugs which selectively accumulate pharmacologically active compounds in hyperactivated cells. In accordance with another object of the invention, the pharmacologically active compound is released from the prodrug in response to enzyme activity within the target cells. In accordance with vet another aspect of the invention, the pharmacologically active compound, selectively accumulated in a cell characterized by a relatively raised level of enzyme activity therein, is trapped in the cell and therefore exhibits an enhanced desired activity therein.

The present invention accordingly provides in one aspect, a prodrug which is a covalent conjugate of a pharmacologically active compound and an intracellular transporting adjuvant, characterized by the presence of a covalent bond which is scission-sensitive to intracellular enzyme activity.

It will also be self-evident that a similar concept can be applied to the treatment of conditions or diseases other than those related to the intramolecular level or $Ca^{2+}$ ions. By way of example, if the active entity incorporated in the prodrug molecule is a protein kinase inhibitor, after administration of the prodrug the inhibitor would be accumulated in a cell exhibiting abnormal proliferation, thus providing potentially an important tool for use in antitumor therapy.

In accordance with one object of the invention, there are provided prodrugs which selectively accumulate pharmacologically active compounds in hyperactivated cells. In accordance with another object of the invention, the pharmacologically active compound is released from the prodrug in response to enzyme activity in the targeted cells. In accordance with yet another object or the invention, the pharmacologically active compound, selectively accumulated in a cell characterized by a relatively raised level of enzyme activity therein, is trapped in the cell and therefore exhibits an enhanced desired activity therein.

The present invention accordingly provides in one aspect, a prodrug which is a covalent conjugate of a pharmacologically active compound and an intracellular transporting adjuvant, characterized by the presence of a covalent bond which is scission-sensitive to intracellular enzyme activity.

In another aspect, the present invention provides a technique for treating a condition or disease in a human, related to supranormal intracellular enzyme activity, which comprises administering to a human having such condition or disease, a pharmaceutically acceptable cell membrane permeable prodrug, the prodrug being a covalent conjugate of a cell membrane impermeable pharmacologically active compound and an intracellular transporting adjuvant, characterized by the presence of a covalent bond which is scission-sensitive to intracellular enzyme activity, such that the bond is broken in response to such activity, whereby the pharmacologically active compound accumulates selectively within cells having supranormal intracellular enzyme activity, the prodrug being administered in an amount effective for reducing the supranormal enzyme activity.

In yet another aspect, the invention provides use for the manufacture of a medicament for treating a condition or disease in a human related to supranormal intracellular enzyme activity, by selectively accumulating a cell membrane impermeable pharmacologically active compound within cells having such activity, of a pharmaceutically acceptable cell membrane permeable prodrug, which is a covalent conjugate of the pharmacologically active compound and an intracellular transporting adjuvant, and is characterized by the presence of a covalent bond which is scission-sensitive to intracellular enzyme activity, such that the bond is broken in response to such activity.

BRIEF DESCRIPTION OF THE DRAWINGS

The invention will be understood and appreciated more fully from the detailed description below, in conjunction with the drawings, in which.

DETAILED DESCRIPTION OF THE INVENTION

Figure 1A:
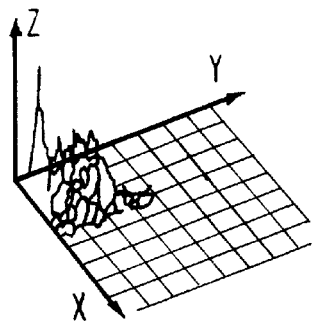
FIG. 1 is a graphical illustration of the effects of a compound, in accordance with an embodiment of the present invention, on intracellular free $Ca^{2+}$ level in human lymphocytes.
Figure 1B:
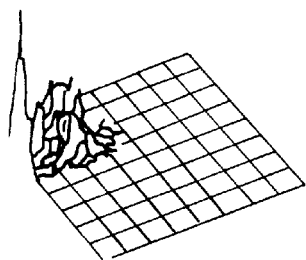
Figure 1C:
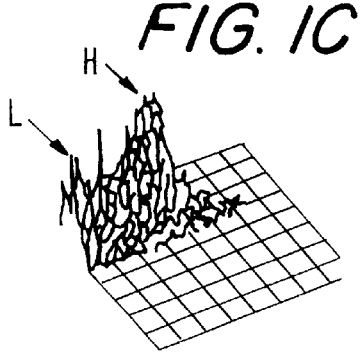
Figure 1D:
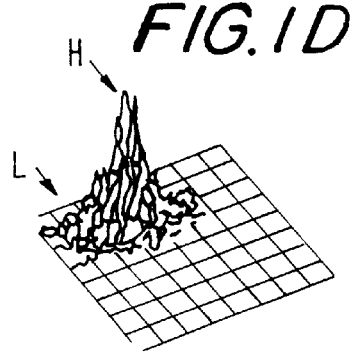
Figure 1C:
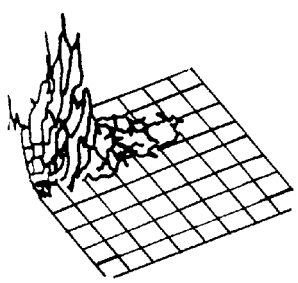
Figure 1D:
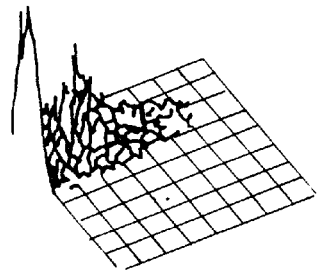

The pharmacologically active compound may be e.g. a pharmacologically active carboxylic acid, when the adjuvant may comprise (e.g.) at least one pharmaceutically acceptable alcohol which is selected from glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters or lysophosphatidic acids, lyso-plasmalogens, lysophospholipids, lysophosphatidic acid amides, glycerophosphoric acids, lysophophatidal-ethanolamine, lyso-phosphatidylethanolamine and N-mono- and N,N-di-($C_{1-4}$)-alkyl and quaternated derivatives of the amines thereof. Exemplary of pharmacologically active carboxylic acids are branched-chain aliphatic carboxylic acids (e.g. valproic acid), salicylic acids (e.g. acetylsalicylic acid), steroidal carboxylic acids (e.g. lysergic and isolysergic acids), mono-heterocyclic carbocylic acids (e.g. nicotinic acid) and poly-heterocyclic carboxylic acids (e.g. penicillins and cephalosporins). While pharmacologically active carboxylic acids are particularly described herein, as exemplary of the active compounds which may be conjugated with an intracellular transporting adjuvant, the invention is not limited thereto. Thus, by way of further example, it is entirely within the concept or the present invention to conjugate therapeutically active nucleic acids (including RNA and DNA) or fragments thereof with an intracellular transporting adjuvant.

In a non-limitative embodiment, the prodrug according to the invention includes a calcium chelating agent, and may thus be of potential use for treating diseases or conditions which are related to an unduly high level of intracellular $Ca^{2+}$ ions. In a particularly preferred embodiment, the prodrug contains at least one covalent bond between the pharmacologically active compound and the intracellular transporting adjuvant, which covalent bond is scission-sensitive to intracellular enzyme activity, with the consequence that the greater part of the prodrug molecules will move freely in and out of normal cells without scission of such bond, whereas in the cells possessing the supranormal enzyme activity only, the scission-sensitive bond in a high proportion of prodrug molecules entering the cells will break, thus accumulating intracellularly, and trapping within the abnormal cell, the pharmacologically active compound, since the latter is cell membrane impermeable. Persons skilled in the art will appreciate in what manner the concept of the invention may be applied to conditions and diseases which are not necessarily related to an intracellular excess of calcium ions, so that in such other cases, the prodrug will incorporate an active compound which is not a calcium chelator but which will possess other desired pharmacological activity.

The prodrug which includes a calcium chelating agent is, e.g., a partially or totally esterified carboxylic acid, which is an ester of:

(a) a pharmaceutically acceptable chelating agent for calcium having the formula $(HOOC-CH_2-)_2-N-A-N-(-CH_2COOH)_2$ where A is saturated or unsaturated, aliphatic, aromatic or heterocyclic linking radical containing, in a direct chain link between the two depicted nitrogen atoms, 2–8 carbon atoms in a continuous chain which may be interrupted by 2–4 oxygen atoms, provided that the chain members directly connected to the two depicted nitrogen atoms are not oxygen atoms, with (b) a $C_{3-32}$ pharmaceutically acceptable alcohol containing 1–3 OH radicals (e.g., such a $C_{3-6}$ alcohol, or e.g. a $C_{7-32}$ secondary monohydric alcohol);

and salts with alkali metals of the partially esterified carboxylic acids, as well as acid addition salts of such of the esterified carboxylic acids as contain one or sore potentially salt-forming nitrogen atoms.

The ester of the preceding paragraph may be one in which the linking radical A is a member selected from the group consisting of —$(CH_2CH_2)_m$— where m=1–4, in which 2–4 of the carbon atoms not attached to nitrogen may be replaced by oxygen atoms, and —CR—CR—O—$CH_2CH_2$—O—CR'=CR'—, where each of the pairs of radicals R—R and R'—R', together with the attached —C=C— moiety, complete an aromatic or heterocyclic ring containing 5 or 6 ring atoms, the ring completed by R—R being the same as or different from the ring completed by R'—R'.

In particular embodiments, the linking radical A nay be, e.g., selected from —$CH_2CH_2$— and —$CH_2CH_2$—O—$CH_2CH_2$—O—$CH_2CH_2$—; or it may be e.g. —CR=CR—O—$CH_2CH_2$—O—CR'=CR'—, where each of the pairs of radicals R—R and R'—R', together with the attached —C=C— moiety, complete an aromatic or heterocyclic ring which is selected from the group consisting of furan, thiophene, pyrrole, pyrazole, imidazole, 1,2,3-triazole, oxazole, isoxazole, 1,2,3-oxadinzole, 1,2,5-oxadiazole, thiazole, isothiazole, 1,2,3-thiadiazole, 1,2,5-thiediazole, benzene, pyridine, pyridazine, pyrimidine, pyrazine, 1,2,3-triazine, 1,2,4-triazine, and 1,2-,1,3- and 1,4-oxazines and thiazines, the ring completed by R—R being the same as or different from the ring completed by R'—R'. In a particularly preferred embodiment, the linking radical A is —CR=CR—O—$CH_2CH_2$—O—CR'=CR'—, where each of the pairs of radicals R—R and R'—R', together with the attached —C=C— moiety, completes the same or different rings selected from unsubstituted and substituted benzene rings, in which substituted benzene rings contain 1–4 substituents selected from the group consisting of $C_{1-3}$-alkyl, $C_{1-3}$-alkoxy, F, Cl, Br, I and $CF_3$, or a single divalent substituent which is —O—$(CH_2)_n$—O— and n=1–3.

It is presently preferred that the calcium chelating agent incorporated in the prodrug is selected from ethylene-1,2-diamine-N,N,N',N'-tetraacetic acid, ethylene-1,2-diol-bis-(2-aminoethyl ether)-N,N,N',N'-tetraacetic acid and 1,2-bis-(2-aminophenoxy)ethane-N,N,N',N'-tetraacetic acid.

As mentioned above, $C_{3-32}$, e.g. $C_{3-6}$, alcohol referred to above contains 1–3 OH radicals. When 2 OH radicals are present, one of them may be esterified or otherwise derivatized, and when 3 OH radicals are present, either 1 or 2 of the OH radicals nay be esterified or otherwise derivatized. Any carbon atoms in the esterifying or otherwise derivatizing group(s) are not counted for the purpose of the e.g. 3 to 6 carbon atoms which may be contained in the pharmaceutically acceptable alcohols. Thus, these alcohols may comprise, e.g., at least one member of the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lysoplasmalogens, lysophospholipids, lysophosphatidic acid amides, glycerophosphoric acids, lysophophatidalethanolamine, lysophosphatidylethanolamine and the N-mono-$C_{1-4}$-alkyl, N,N-di-$C_{1-4}$-alkyl and quaternary ammonium derivatives of such of the foregoing as are amines. An example of a $C_{7-32}$ secondary alcohol is 1-myristylmyristyl alcohol.

The person skilled in the art will appreciate that the prodrug of the present invention can be tailored in such a manner that the desired pharmacologically active entity is released by action of the enzyme known to be the source of enzyme hyperactivity in the condition or disease being treated. For example, membrane-associated calcium-independent plasmalogen-selective $PLA_2$ activity has been found to increase over 400% during two minutes of global ischemia (P<0.01), was greater than 10-fold (near to the maximum) after only five minutes of ischemia, and remained activated throughout the entire ischemic interval examined (up to 60 minutes), see Ford et al. J. Clin. Invest., 1991, 88(1): 331–5. These facts suggest attaching the pharmacological active entity to the 2-position in a glycerophosphoric acid derivative, and that use of a lysoplasmalogen may possibly be more effective as the intracellular transporting adjuvant, to which the active entity is attached covalently, than a lysophospholipid.

Any events (e.g. cytotoxic chemicals, physical stimuli and infective agents) causing damage of the cell membrane can trigger a cascade leading ultimately to a condition which mimics ischemia (Robbins et al, Pathological Basis for Disease, 1984, p. 10, W. B. Sanders Co.). The present invention will potentially be of use for protecting cells in these circumstances, by introduction of a calcium-chelator intracellularly. In this connection, it is noted that the antitumor drug Adriamycin, which has been reported to inhibit Na-Ca exchange and to overload the sarcoplasm with calcium, could induce contractile heart failure; this would be consistent with the hypothesis that calcium overload, in absence of ischemia, can leave behind long-lasting contractile dysfunction (Kusuoka et al, J. Cardiovasc. Pharmacol., 1991, 18(3): 437–44).

As indicated above, the concept of the present invention is not restricted to the treatment of conditions or diseases related to the intramolecular level of $Ca^{2+}$ ions, so that the materials used in practising the invention are not restricted to calcium chelators. Thus for example, the pharmacologically active compound-may be e.g. an antiepileptic compound such as valproic acid. In this connection, it is contemplated that application of the present invention in this embodiment would enable a much lower effective dose of valproic acid to be used than is otherwise the case, thus potentially substantially reducing the occurrence of undesired side-effects. In principal, any of the range of alcohols, and examples thereof, mentioned above in connection with esterification of calcium chelators may also be applied to the esterification of valproic acid in accordance with the concept of the present invention. In a non-limiting embodiment, valproic acid may be esterified with, e.g., 1-heptanoyl-sn-glycero-3-phosphorylcholine.

In another particular embodiment, the pharmacologically active compound incorporated in the prodrug of the invention is a protein kinase inhibitor. Where the protein kinase inhibitor is a carboxylic acid, the prodrug may be e.g. an ester thereof with a pharmaceutically acceptable alcohol such as glycerol, $C_{3-20}$ fatty acid monoglycerides. $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lysoplasmalogens, lysophospholipids, lyso-phosphatidic acid amides, glycerophosphoric acids, lysophophatidalethanolamine, lysophosphatidylethanolamine and N-mono- and N,N-di-($C_{1-4}$)-alkyl and quaternated derivatives of the amines thereof. Such a carboxylic acid is e.g. protein kinase inhibitor K252b from Nocardiopsis sp.

Where the protein kinase inhibitor contains an amine group with a replaceable N-linked hydrogen atom, the prodrug may be e.g. an amide thereof with a phosphoric acid derivative selected from glycerophosphoric acids, O-acylated or etherified glycerophosphoric acids, and monoacylated monoetherified glycerophosphoric acids. Such protein inhibitors are e.g. isoquinoline-5-sulfonamide N-substituted by an acyclic or heterocyclic aminoalkyl radical such as $NHCH_2CH_2NHCH_3$ and 2-methylpiperazin-1-yl. Where the protein kinase inhibitor contains at least one phenolic hydroxy group, the prodrug may be e.g. an ester thereof with a phosphoric acid derivative selected from glycerophosphoric acids, O-acylated glycerophosphoric acids, etherified glycerophosphoric acids, and monoacylated monoetherified, glycerophosphoric acids. Such a protein kinase inhibitor is e.g. 4',5,7-trihydroxyisoflavone.

When selecting the intracellular transporting adjuvant for the purposes of the present invention, the skilled person will of course take into consideration the necessity for avoiding such adjuvants, e.g. certain 1,2-diauylglycerols, which are activators of protein kinase C (see Lapetine et al. J. Biol. Chem., 1985, 260: 1358 and Boynton et al. Biochem. Biophys. Res. Comm., 1983, 115: 383). or intracellular transporting adjuvant which are likely to give rise to undesirable products such as these in the cell.

DETAILED DESCRIPTION OF THE PRESENTLY PREFERRED EMBODIMENTS

EXAMPLE 1

Preparation of Prodrug-1 and Prodrug-2

Introduction

"Prodrug-1" is the name used herein to denote a 1:1 ester of 1,2-bis-(2-aminophenoxy)ethane-N,N,N',N'-tetraacetic acid (BAPTA) with the choline derivative $ROCH_2$—CH(OH)—$CH_2O$—($PO_2$)—$OCH_2{}^+N(CH_3)_2$, where R is heptanoyl. BAPTA is a calcium chelator, to which the human cell membrane is normally impermeable, whereas the cell membrane is permeable to prodrug-1, which is not a calcium chelator per se. The carbozylic ester links in prodrug-1 are digestible by $PLA_2$, so that activated cells such as IgE lymphocytes should exhibit a selective intracellular accumulation of BAPTA, compared to the unactivated cells, with the result that the $[Ca^{2+}]_i$ level in the activated cells should be reduced when compared with unactivated cells. "Prodrug-2" is the 1:2 ester of BAPTA with the depicted choline derivative.

Procedure.

(a) Diheptanoyl-L-α-lecithin

In a dry 3-neck 500 ml flask equipped with oil-sealed stirrer, $CaCl_2$ tube and dropping funnel, were placed 100 ml 5 mm diameter glass beads and 11.0 g (0.01 mole) of $CdCl_2$ adduct of synthetic L-α-glycerophosphoryl-choline. The flask was immersed in an ice-water bath, and to the rapidly-stirred mixture there was added a thin stream of 29.7 g (0.2 mole) freshly prepared heptanoyl chloride dissolved in 60 ml chloroform*, followed by 11 ml (0.14 mole) anhydrous pyridine dissolved in 100 ml chloroform*(*anhydrous, alcohol-free). After 30 minutes, the bath temperature was raised to 25° C. and stirring continued for 2 hours. The reaction mixture was poured through a filter-less Buchner. the glass beads washed with 3×50 ml chloroform and the combined filtrates clarified by centrifugation. The supernatant was concentrated under reduced pressure, the residue kept for several hours at 0.1 mm vacuum and bath temperature 30–35° C. to remove most excess pyridine, and was then stirred with 500 ml anhydrous acetone for 10 minutes, and centrifuged. The precipitate was treated similarly with 2×100 ml anhydrous acetone and 2×100 ml anhydrous ether.

The residual solid material was dried under reduced pressure and freed of the last traces of cadmium chloride and pyridine hydrochloride, by dissolving in 200 ml of a 5:4:1 by volume mixture of chloroform/methanol/water, and passing the solution through a 120 cm long×2.5 cm diameter column containing an equivolume mixture of Amberlites IR-45 and IRC-50. The column was washed with 500 ml of the same chloroform/methanol/water mixture, the combined effluents were concentrated to dryness under reduced pressure from a bath at 40–45° C. and the residue dried at 0.1 mm vacuum and 45° C. The crude product was purified by precipitation from a solution in 50 ml chloroform, with 150 ml acetone, centrifugation and recrystallization of the precipitate. 2.3 g (47.6%) from chloroform and ether. (Dioctanoyl-L-α-lecithin can be prepared similarly.)

(b) 1-Heptanoyl-sn-3-glycerophosphorylcholine

A solution of the product of part (a) (1.2 mmol) in a mixture of ether (196 ml) and methanol (12 ml) was stirred vigorously in presence of $(HOCH_2)_3C$—$NH_2.HCl$ (50 ml of 0.1M, pH 8.7) containing $CaCl_2$ (0.72 mM) and 5 mg of crude rattle snake venom (*Crotalus adamanteus*) as a source of phospholipase $A_2$, at 37° C. for 3 hours. The reaction was monitored by TLC (70:25:4 by volume chloroform/methanol/water). After completion of reaction, the organic layer was separated, and the aqueous layer was washed with ether and then lyophilized. The residue was extracted with 2:1 by volume chloroform/methanol and centrifuged. On evaporation of the clear supernatant, the title product was obtained in 90% yield; Thin layer chromatography using 70:25:4 by volume chloroform/methanol/water showed that it was free from starting material and heptanoic acid. Any fatty acid in the product can however be remove by crystallization from ethanol-ether. Note: this is a general method for scission of the glycerol-2-ester bond. (Octanoyl-sn-3-glycerophosphoryl-choline can be prepared-similarly.)

(c) Prodrug-1 and Prodrug-2

A solution of the product of part (b) (0.5 g, 1.04 mmol) in chloroform (15 ml, freshly distilled over $P_2O_5$) was added to a solution of BAPTA (0.495 g, 1.03 mmol for the monoester Prodrug-1, or 0.248 g, 0.51 mmol for the diester Prodrug-2), N,N'-dicyclohexyl-carbodiimide (0.214 g. 1.03 mmol) and 4-dimethylaminopyridine (0.025 g, 0.202 mmol) and $HCONMe_2$ (20 ml, freshly distilled over $CaH_2$) under a nitrogen atmosphere, and the mixture was stirred at room temperature for two days. The reaction was monitored by TLC (65:35:5 by volume chloroform/methanol/water). The precipitate was removed by filtration, the filtrate was concentrated by evaporation in vacuo at 35° C. and the residue was dissolved in 2:1:2 by volume chloroform/isopropanol/water). The organic layer was separated, dried ($Na_2SO_4$) and then passed through a 20 cm long×1.8 cm diameter column of silicic acid (Bio-Sil-HA). The column was thoroughly washed with chloroform until free from BAPTA (TLC) and then eluted with a gradient of chloroform/methanol (1:1 by volume) to pure methanol, the elution being monitored by TLC. The eluted fractions were combined and concentrated by evaporation. The desired title product (i.e. Prodrug-1 or Prodrug-2, depending on the number of molar equivalents of BAPTA used) was crystallized from ether and dried in vacuo over $P_2O_5$ at 30° C.: yield 0.3 g (30%). It will be apparent that the corresponding triester or tetraester may be obtained by varying appropriately number of molar equivalents or BAPTA. (The analogous octanoyl esters are prepared similarly.)

EXAMPLE 2

Application or Prodrug-1 for reduction of the intracellular calcium level in hyperactivated cells Method Intracellular free $[Ca^{2+}]_i$ content was monitored by flow cytometry using the $Ca^{2+}$-sensitive dye fluo-3/AM (Molecular Probe Inc., Or.)(see Minta et al, 1989; Kao et al, 1989). Cells obtained from donor blood and those from the blood of an asthmatic patient were further washed twice in DMEM and resuspended to a concentration or $10^7$ cells/ml. Fluo-3/AM (1 mM) was prepared in DMSO augmented with the nonionic surfactant Pluronic P-127 (Wyandotte Corp., MI). Aliquots or fluo-3/AM stock solution were added to cell suspensions in DMEM/HEPES at a final concentration of 3 μM (loading buffer). Loading was allowed to proceed for 30 min. at 37° C. and continued for 1 hour at 23° C. with gentle agitation. Cells were then adjusted to desired concentrations using fresh DMEM/HEPES, supplemented with 2% horse serum. Autofluorescence was eliminated by setting the threshold sensitivity above the levels obtained in absence of dye. Fluorescence intensity data was collected from 5000 single cells and values were expressed as arbitrary fluorescence units. Prodrug-1 (1 mM) was prepared in DMSO and added when appropriate in final concentration 3 μM to the cells for 5 min. prior to calcium treatment.

Results

Lymphocytes from donor blood and from the blood of an asthmatic patient were exposed to prodrug-1. Accumulation of the liberated BAPTA chelator within the cell was estimated by measurement of $[Ca^{2+}]_i$, by flow cytometry using fluo-3/AM as described, above. The results are documented in FIG. 1. in which the $[Ca^{2+}]_i$ levels are shown in:

normal lymphocytes (panel A);
normal lymphocytes treated with prodrug-1 (panel B);
lymphocytes from asthmatic patient (panel C);
lymphocytes from asthmatic patient stimulated with IgE (panel D);
lymphocytes from asthmatic patient) (panel C');
treated with prodrug-1} and
lymphocytes from asthmatic patient stimulated with IgE} (panel D')
treated with prodrug-1}.

It is noted that lymphocytes from an asthmatic patient have a double repartition according to the $[Ca^{2+}]_i$ level (panel C). About 50% of the cells exhibit a high $[Ca^{2+}]_i$ level indicating cell hyperactivation, while the second part of the population is similar to the normal one (compare panel A). In the case of panels C' and D', where the cells have been treated with prodrug-1, the population of hyperactivated cells is back to normal, while the population of non-activated cells remains intact (compare panel C). The data demonstrate that prodrug-1 provides selective accumulation of the chelator within activated, but not in non-activated cells.

EXAMPLE 3

Prodrugs of Potential Application in the Treating Tumors

Introduction

In this Example, there are presented a number of illustrative embodiments of the present invention in which a prodrug incorporates a protein kinase inhibitor. After, administration of the prodrug, the inhibitor would be accumulated in a cell exhibiting abnormal proliferation, thus providing potentially an important tool for use in antitumor therapy.

(i) The compound $QSO_2\tilde{N}$ where Q=5-isoquinolyl and $\tilde{N}$=NHCH$_2$CH$_2$NHCH$_3$, is a selective inhibitor of cAMP-dependent protein kinase: Hidaka et al, Biochemistry, 1984, 23: 5036, and Tash et al, J. Cell Biol., 1986, 103: 649. Similarly, the compound QSO$_2$ $\tilde{N}$ where Q=5-isoquinolyl and N=2-methylpiperazin-1-yl, is a potent inhibitor of cyclic nucleotide dependent protein kinase and protein kinase C: Hidaka et al, loc cit, and Kikuchi et al, Nucl. Acid Res., 1988, 16: 10171. These compounds can be covalently conjugated to an intracellular transporting adjuvant by methods known to persons of the art, e.g. illustratively:

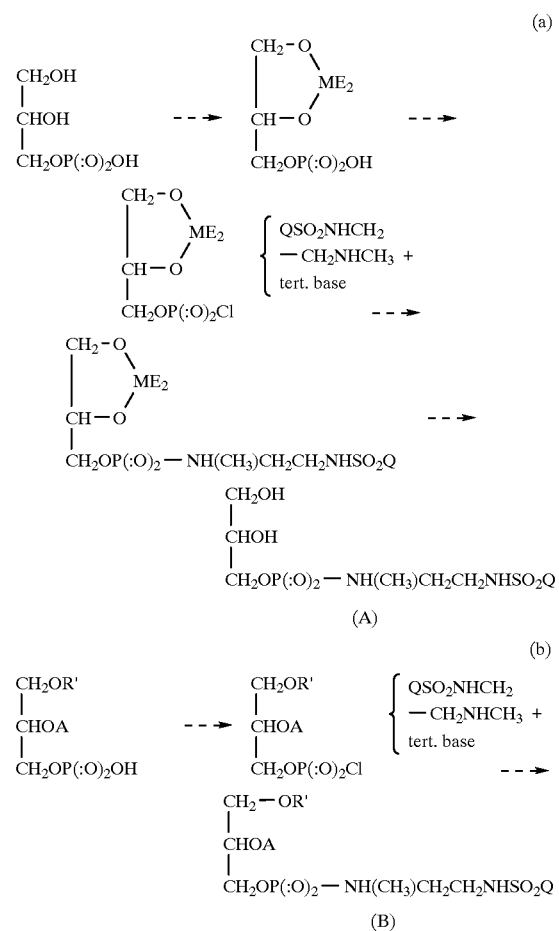

In scheme (b), R is an aliphatic hydrocarbon group such as is found in plasmalogens (or it may be inserted in a conventional synthetic procedure) and A is an aliphatic acyl radical, e.g. lauroyl, myristoyl, palmitoyl, stearyl and oleyl.

The compound $QSO_2\tilde{N}$ where Q=5-isoquinolyl and $\tilde{N}$=2-methylpiperazin-1-yl, may be attached in a similar manner by means of the piperazine $N^4$ atom.

It would be expected that the P—N bond in prodrugs (A) and (B) depicted above would be scission-sensitive to enzyme PLD, thus releasing the described protein kinase inhibitors intracellularly, and accumulating these inhibitors in cells having a supranormal level or PLD.

(ii) 4',5,7-trihydroxyflavone is an inhibitor of tyrosine specific protein kinase: Akiyama et al, J. Biol. Chem., 1987, 262: 5592. This compound can be conjugated to an intracellular transporting adjuvant by methods (a) and (b) described in part (i), above. The illustrative conjugates would have structures (C) & (D):

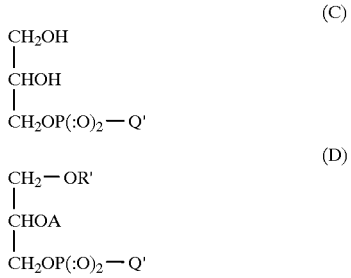

where R' and A have the meanings given above and Q' is the residue of 4',5,7-trihydroxyisoflavone from which one phenolic hydrogen atom has been removed and which is thus attached to the rest of the molecule by an 0 atom forming a P—O bond. It would be expected that this P—O bond in prodrugs (C) and (D) depicted above would be scission-sensitive to enzyme PLD, thus releasing the described protein kinase inhibitors intracellularly, and accumulating these inhibitors in cells having a supranormal level of PLD.

(iii) Protein kinase inhibitor K252b from Nocardiopsis sp. is a carboxylic acid believed to have the following formula:

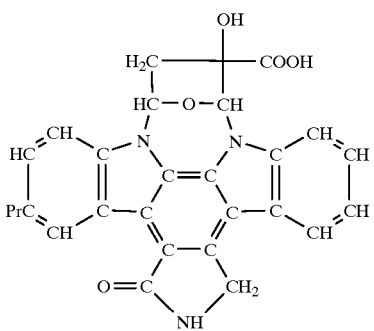

This compound can be conjugated to an intracellular transporting adjuvant, e.g., by the method described in Example 1. above. Exemplary conjugates are esters of the carboxylic function in the above formula, with e.g. heptanoyl-sn-3-glycerophosphoryl-choline or octanoyl-sn-3-glycerophosphoryl-choline.

EXAMPLE 4

Preparation and Biological Properties of DP16

"DP16" denotes herein to denote a 1:1 ester of BAPTA with the choline derivative

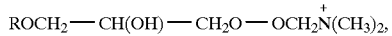

where R is hexadecanoyl. DP16 was prepared according to the method described in Example 1.

Introduction to Evaluation of DP16 in Relation to Ischemia

Bilateral occlusion of the common carotid arteries is the simplest and most direct approach for inducing global ischemia. In the rats there is almost 64% mortality in 24 h later. The causes of mortality are largely brain swelling (edema) and focal lesions (infarcts). Global ischemia is achieved by isolation of the common carotid artery through and incision on the ventral surface of the neck. The salivary glands are moved laterally and the carotid sheath exposed. Both the vagus and sympathetic nerves are separated from the common carotid artery, which is then permanently ligated. Sprague-Dawley rats (250–300 g) were anesthetized with halathane or by intramuscular injection of 0.1 ml Ketamine (0.1 g/ml, Park Davis, UK) and 0.1 ml Rompun (2%, Bayer, FRG) per 300 g body weight. DP16 was administered i.p., (0.001–0.1 mg/kg) when appropriate following the artery legation. Every experimental and control group included 14 male rats. Statistical analysis was performed according t criteria.

Experimental Details and Results of Ischemia Testing

Embolic Stroke

Sprague-Dawley rats (300 g) are anesthetized with halathane. The right common carotid artery is exposed and the external carotid and pterygopalatine arteries are ligated with No. 0 silk thread. The common carotid artery is cannulated with a plastic tube previously filled with heparinized saline. The canula is then injected (0.5 ml gas-tight Hamilton syringe) with suspension of the spheres, followed by push of 0.5 ml saline. The common carotid artery is then permanently ligated. The polystyrene 15 $\mu$m spheres are prepared in 0.05% Tween-80 in normal saline followed by 5 min. of full power sanitation. A 100 $\mu$l aliquot is taken and immediately transferred to the syringe.

Ischemia Fetal Brain Model

Sprague-Dawley pregnant rats were used at 20 days gestation. Animals were anesthetized by intramuscular injection of 0.1 ml Ketamine (0.1 g/ml. Park Davis, UK) and 0.1 ml Rompun (2%, Bayer, FRG) per 300 g body weight. An abdominal incision was performed and the two uterine horns were exposed and kept moist throughout the surgery. Intracerebral injection of 1–2mCi/2 ml [$^3$H]arachidonic acid (Na+, 240 mCi/mmol from New England Nuclear, Boston, Mass.) and/or 1.5 mCi/2 ml [$^{14}$C]palmitic acid (Na+, 819 mCi/mmol from Amersham, Searle. UK) in isotonic salt solution containing NaHCO$_3$ (1.32 g%), into the embryos was performed through the uterine wall into the fontanellae. Custom made syringes (33 gauge, 0.375" length from Hamilton, Reno, Nev.) were used to reduce brain edema. After injection fetuses were returned to the abdominal cavity for maintenance at physiological temperature. After 1 h they were subjected to blood flow restriction for 20 min. (restriction session) by clamping the blood vessels in the placenta manifold. Whenever desired, circulation was restored for 30 min. by removal of the clamps (reperfusion session). At all times both restricted and sham-operated fetuses were maintained in the abdominal cavity before surgical delivery. After delivery through a transverse cut in the uterus, viable fetuses with no apparent edema were killed without delay, and excised fetal brains were immediately homogenized in suitable organic solvents for further treatment.

Fetuses Cerebral Hemispheres Model

Fetuses were removed from the uterine horns in a viable state and their cerebral hemispheres were dissected within 15 sec after decapitation. The cerebral hemispheres freed of blood and meninges were separated and each (50±2.5 mg) was placed in a well of a 24-well Falcon culture dish. Tissue was quickly washed twice in cold Dulbecco's Modified Eagle Medium (DMEM. Grand Island Biol. Co) and then incubated at 37° C. in 0.6–1.2 ml DMEM flushed with oxygen and supplemented with various additives. Aliquots of incubation medium (0.1 ml) were taken for eicosanoid determination by a radioimmunoassay (RIA) technique. After acidification with 5 ml formic acid, 0.1 ml of isopropanol and 0.5 ml diethylether were added. After mixing and low speed centrifugation (2500×g, 5 min.) the organic layer was collected and dried under a stream of nitrogen. The resulting residue was dissolved in 0.1 ml sodium phosphate buffer pH 7.4, containing 0.1% bovine serum albumin. Samples were incubated overnight at 4° C. with the appropriate polyclonal antiserum, and $^3$H-labeled tracer (4000 cpm/tube) in a final volume of 0.3 ml. Unbound material was precipitated with 0.3 ml dextran-coated charcoal (Pharmacia, Sweden). After centrifugation at 4° C. aliquots of the supernatant (0.4 ml) were transferred to vials and after addition of scintillation liquid samples were counted in a Packard Tricarb scintillation counter. [$^3$H]Arachidonic acid (240 Ci/mmol) (New England Nuclear, Boston. Mass.) dissolved in Isotonic NaHCO$_3$ (1.32% w/v) was injected through the uterine wall and the fontenellae into the embryonic brain. After injection fetuses were returned to the abdominal cavity for maintenance under physiological conditions. After 1 h. fetuses were delivered and immediately sacrificed. Cerebral hemispheres were rapidly excised for subsequent ex vivo incubation or for lipid extraction.

Results

Figure 2:
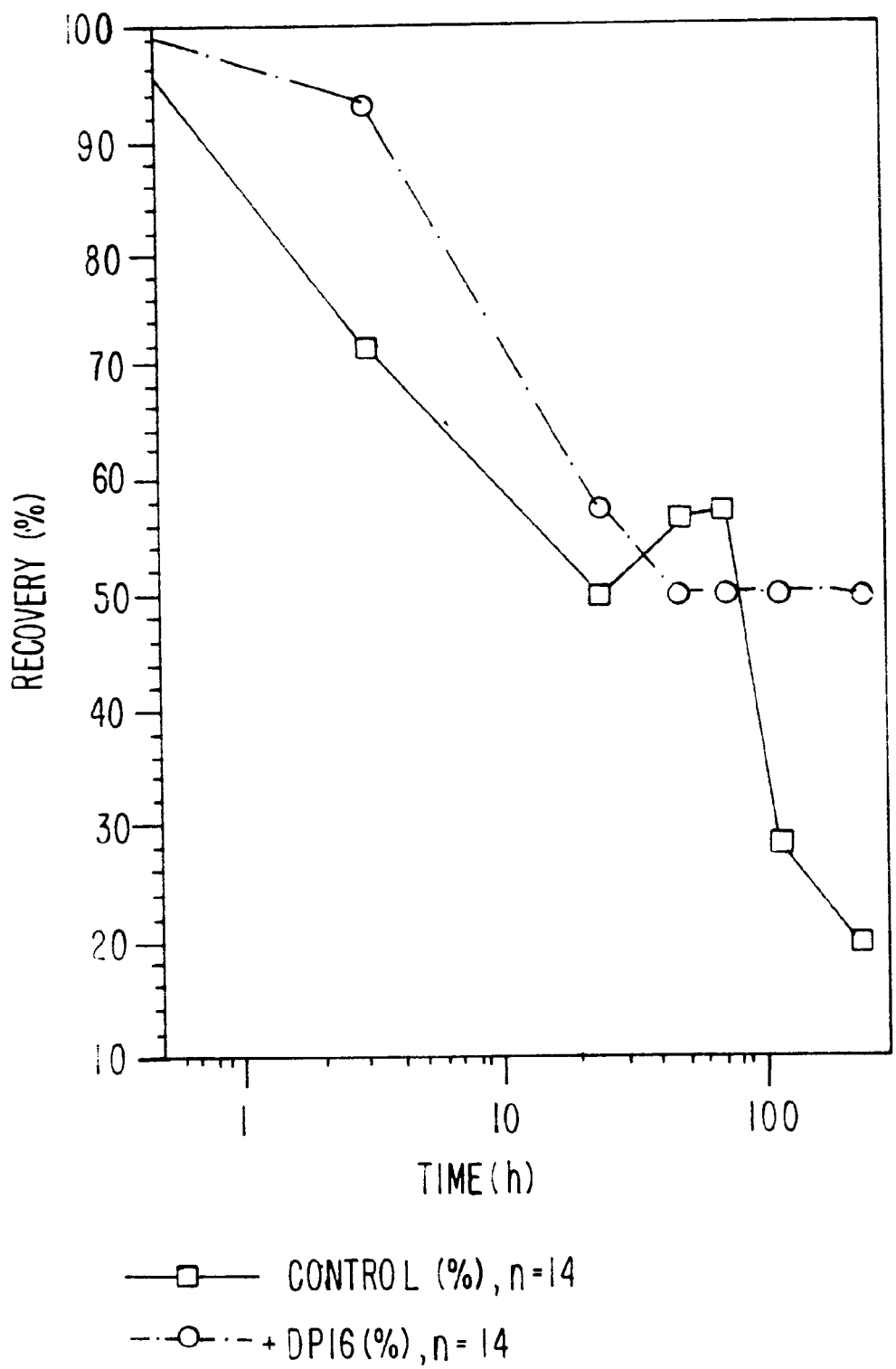
FIG. 2 compares recovery in Global Cerebral Ischemia in presence or absence of a compound in accordance with an embodiment of the invention.

Bilateral Global Cerebral Ischemia causes progressive loss of experimental animals up-to 6–7 days after surgery. As illustrated in FIG. 2. DP16 increases post-ischemic recovery by 250%, compared with control using non-protected rats (p<0.01). This data demonstrates the potential ability of DP 16 to treat otherwise fatal ischemic conditions.

Heart Ischemia—Perfused Heart Model

White rats were sacrificed by cervical dislocation and their hearts were rapidly removed and reperfused at 60 mmHg with modified Krebs-Henselleit buffer utilizing a Langendorff perfused heart model. Hearts were perfused for 10-min. preequlibration interval and were subsequently rendered either global ischemic (zero flow) or continuously perfused for the indicated time. Perfusion were terminated by rapid excision of ventricular tissue and directly submersion into cold homogenization buffer (10 mM imidazole, 10 mM KCl, 0.25 M sucrose [grade 1], pH 7.8) Both the activation of phospholipase A2 and its reversibility during reperfusion were temporally correlated to alterations in myocytic anaerobic metabolism and electron microscopic analyses.

Model of Ventricular Fibrillations Causing by Coronary Occlusion

Dogs (11.6–20.7 kg) were anesthetized and instrumented to measure left circumflex coronary blood flow, left ventricular pressure, and ventricular electrogram. The left anterior descending artery was ligated and an anterior wall myocardial infarction was then produced. All leads to the cardiovascular instrumentation were tunneled under the skin to exit on the back of the animal's neck. Appropriate medicine was given to minimize postoperative pain and prevent inflammation. The ischemia test was performed after 3–4 weeks.

Properties of DP 16 in Relation to the Treatment of Epileptic Disorders

Pilocarpine Based Model of Experimental Epilepsy

Acetylcholine, acetylcholinesterase inhibitors and acetylcholine analogues are effective epileptogenic agents when applied intracerebrally or systematically (see ref. in Leite et al., Neurosci. & Biobeh. Rev., 1990. 14: 511–17). It was demonstrated in different species that systemic administration of muscarinic cholinergic agonists produced electroencephalographic and behavioral limbic seizure accompanied by widespread brain damage resembling topographically that produced by kainic acid and folates and are frequently observed in autopsied human epileptics. Systemic injections of the pilocarpine a potent muscarinic cholinergic agonist, are capable of producing a sequence of behavioral alterations including stirring spells, facial automatisms and motor limbic seizures, that develop over 1–2 hours and build progressively into limbic status and following by general status epilepticus.

Results

Figure 3:
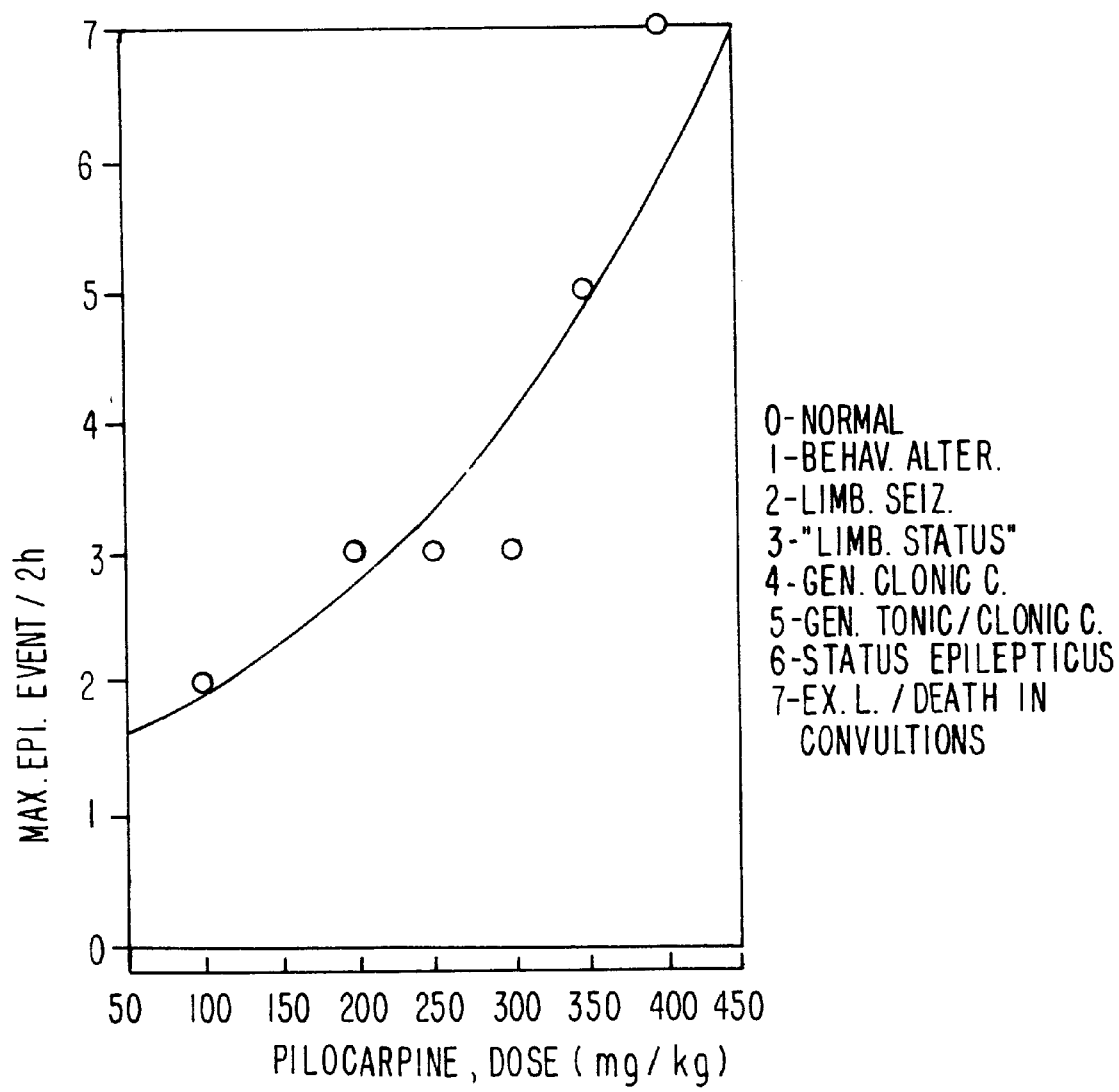
FIG. 3 illustrates the variation with dosage of pilocarpine induced epileptic events.

Immediately following injection of pilocarpine, akinesia, ataxic lurching, facial automatism and heart tremor dominated the animals' behavior. Further development of epileptic events is dose—dependent (FIG. 3). Administration of pilocarpine in doses of 300–350 mg/kg causes appearance of limbic seizures with rearing, forelimb clonus, salivation, intense masticatory jaw movements and falling. Motor limbic seizures commenced after 20–30 min., recurred every 2–8 min and lead to status epilepticus. Increase of the dose of pilocarpine up-to 400 mg/kg abolished limbic seizures and after 15–25 sin of initial behavioral alterations causes fatal general tonic—clonic convulsions. We consider this dose as $LD_{100}$.

Figure 4:
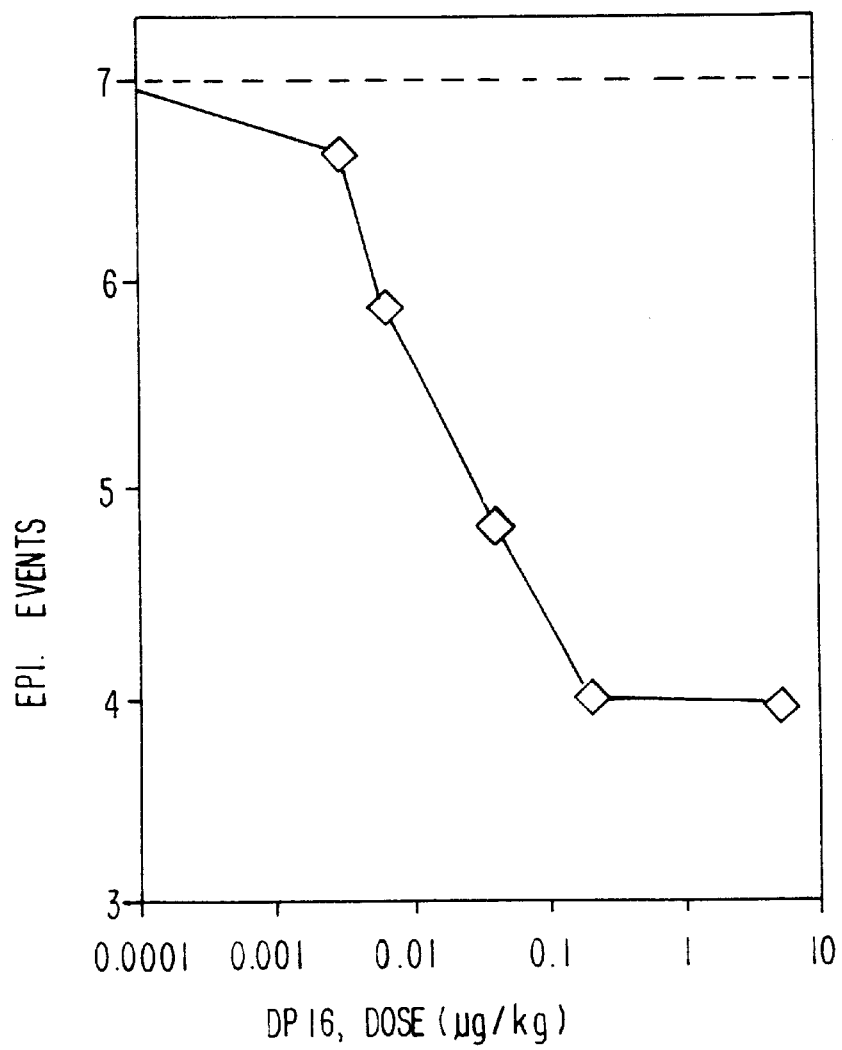
FIG. 4 illustrates the protection against pilocarpine induced epileptic events afforded by a compound in accordance with an embodiment of the invention.

Administration of DP16 prior to pilocarpine prevented death in the animals and decreased epileptiform manifestations. As shown in FIG. 4. DP16 exhibits a therapeutic at doses in the range $10^{-8}$ to $10^{-5}$ mg/kg. For this particular model of epilepsy (pilocarpine 400 mg/kg; rats) the estimated therapeutic index (ET) of DP16 is 0.5 mg/kg/5×$10^{-7}$ mg/kg=1×$10^6$. The data obtained suggest that DP16 is an extremely promising prodrug for the treatment of epileptic disorders.

Pilocarpine and Cardiotoxicity

To types of death were found in rats treated with pilocarpine, firstly due to fatal convulsions and secondly, retarded death not immediately due to epileptic events. We attempted to understand the actual reason of retarded death of rats after pilocarpine-induced convulsions. Under macroscopic autopsy of these animals were seen signs of cardiopulmonary damages: lung edema and hemorrhages, dilated and in same cases deformed hearts. Dyeing or hearts with 0.1% Trypan blue in surviving animals revealed spotted picture of myocardia with areas of intensive dye absorption, i.e., damaged parts, and pale areas, i.e., infarctions. Thus, we can consider that after pilocarpine administration, there developed heart damage, which we term post-pilocarpine-seizure-cardiopathy (PSCP). Studies of PSCP in relation to DP16 evaluation were performed in vivo and in vitro with rats which survived after convulsive and sub convulsive doses of Pilocarpine.

PSCP Experiments

Adult (2–3 months) male Sprague-Dawley rats were used for all experiments. They were fed with standard briquette chow with water ad libitum and were maintained in standard plastic cages (4–5 individuals in each cage) under natural illumination. A pilocarpine-scopolamine epileptic status model (pilocarpine) was performed as described earlier. In a group of 23 rats, pilocarpine was administered i.p. in different doses which ranged from 100 to 400 mg/kg body weight (B/W) for different periods of time; a second group of 17 rats was treated with DP16 prior to pilocarpine administration, wherein the DP16 was injected for 30 min before pilocarpine in the next dose range and its effect was investigated in the ensuing periods.

In vivo ECG (Birtcher-Cardio-Tracer, model 375, USA) in three standard leads were recorded under ketamine anesthesia (3.3 mg/kg Imalgene 100, Rhone Merieux, France and 7 mg/kg Rompun, Bayer-Leverkusen, Germany, i.e.). ECG recordings were made in the period before pilocarpine injections (control), 24 h after pilocarpine administration (acute period) and after relative stabilization of cardiac function, on the 3–14th day after pilocarpine administration. Part of the ECG recordings were made under nembutal anesthesia (35 mg/kg. i.p.) in the period before establishing Langendorff's perfusion isolated heart preparation. Perfusion-Hypoxia-Reperfusion isolated heart model (PHR) was performed with the conventional Langendorff technique (non-recirculating, perfusion system) adjusted to 37° C. in two modifications: 1. under constant Perfusion Pressure (PP)—60 mm Hg; or 2. under constant flow, established after the first 10–15 min perfusion with PP as above, by adjusting flow with help of peristaltic pump (Ismatec SA, Laboratoriumstechnic, Switzerland). In the case of constant PP the volume of effluent flow was measured on electron balance (Precisa 1000C–3000D, Switzerland). In case of constant flow, established at the control period, flow did not change during subsequent experimental periods and PP was recorded frequently. After 30 min of the control period, perfusion was stopped for 30 min and subsequent reperfusion period lasted 30min. Direct ECG were recorded from ventricular apex (lead 1), auriculum (lead 2) and in-between (lead 3). The coronary vessel's perfusion resistance (CVPR) was calculated in arbitrary units as follows: PP/flow/heart weight. Following the protocol above, hearts were subjected to perfusion with the dye Trypan blue (0.1), in order to evaluate cellular damage and infarction.

Results and Discussion

Figure 5:
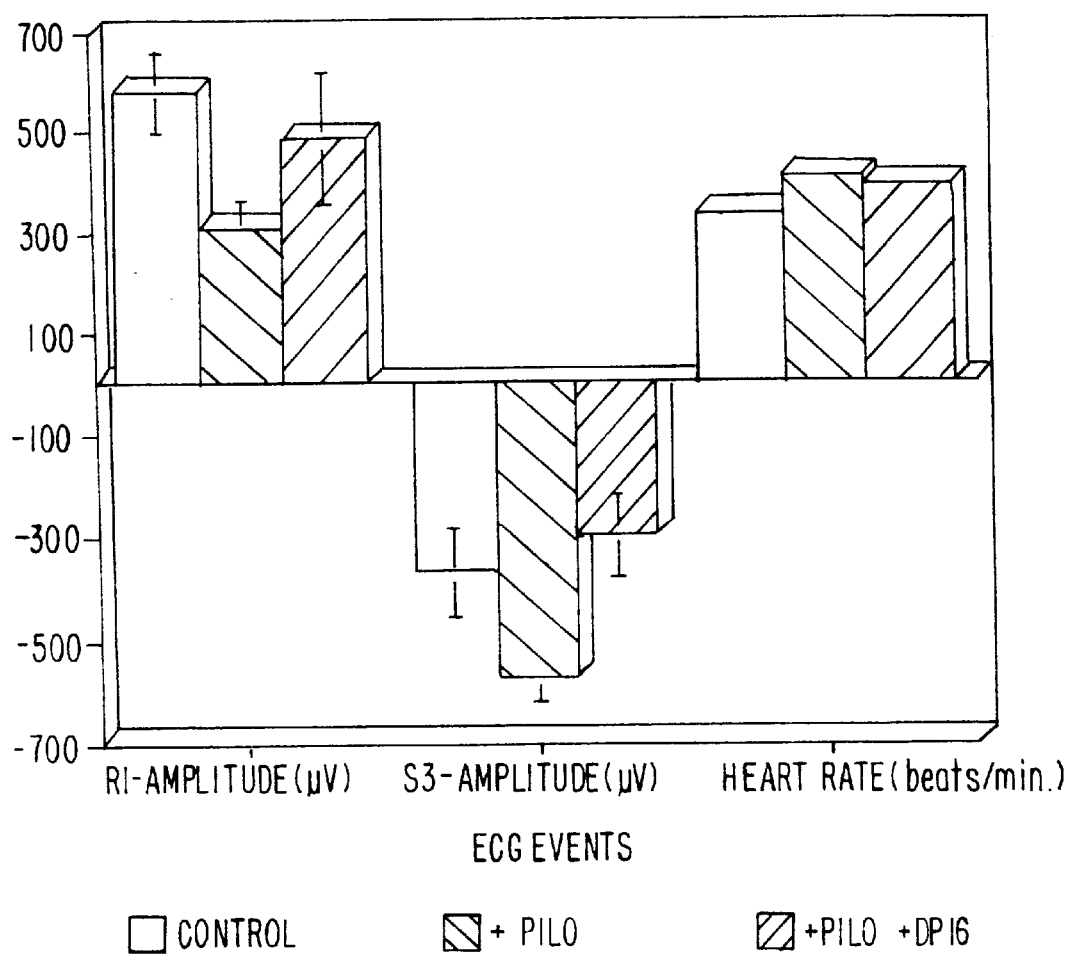
FIGS. 5 and 6 illustrate the protection against long-term alteration of certain cardiac functions, or shift of coronary vessels tone regulation, caused by pilocarpine, afforded by a compound in accordance with an embodiment of the invention.

ECG results in vivo are illustrated in FIG. 5, in which open bars reflect some ECG events, expressed as mean ±SE from individual ECGs in control period. The first group of bars demonstrates ECG changes after pilocarpine injections in an acute stage of PSCP: statistically significant depressions or R- peak are noted under leads 1 and 2 (47% & 16% of control one respectively). DP16 treatment of PSCP normalized electrical activity at the acute stage in 5 out of 7 treated rats. It is known that the amplitude of ECG events are partly connected with the intensity of correspondent physiological processes. Thus, the pilocarpine-induced change of R-wave and its normalization by DP16 may reflect the ability of DP16 to cure ventricular weakness, at least under PSCP. Control rats display relative normalization of R-wave in 3–14 days after pilocarpine. However, R normalization somehow correlated with drastically increased S-wave depth under lead 3 (36%) and lead 2 (61% ).(the last is not yet statistically significant in view of large variability.) Increase of S-wave depth reflected damage of myocardial ischemia & possibly suggesting infarction in Pilocarpine treated control animals. As during the acute stage of PSCP in the phase of stabilization. DP 16 prevents the appearance of ECG alterations noted in control rats. The difference between animals protected with DP16 and those not protected, is statistically significant (p<0.01). In this period PSCP there is marked elevation of Heart Rate as in control Pilocarpine, as in DP16 treated animals. Such tachycardia possibly connected with hemodynamic insufficiency, which is characteristic for infarction pathophysiology. Thus, in vivo ECG investigation during long-term period after Pilocarpine injections revealed definite alteration of cardiac functions (PSCP), which in some animals may be cured by $DP^{16}$-treatment.

Figure 6:
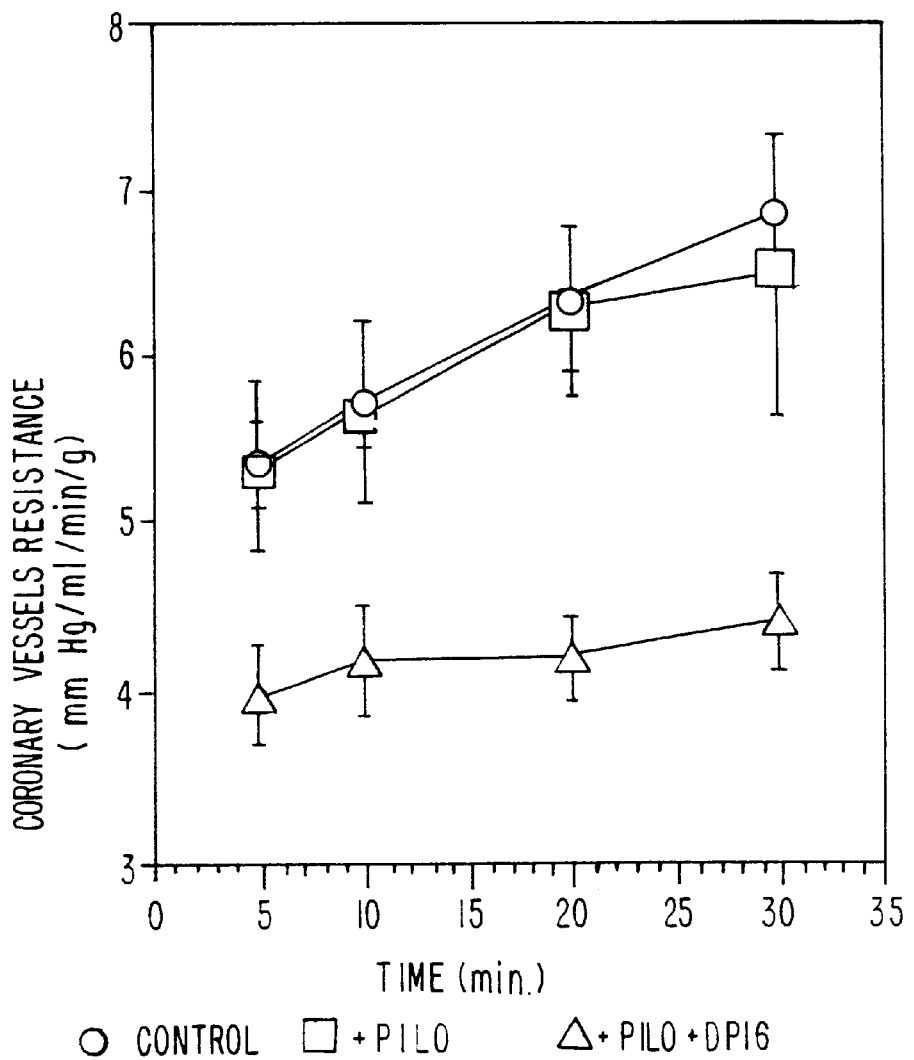
Figure 7:
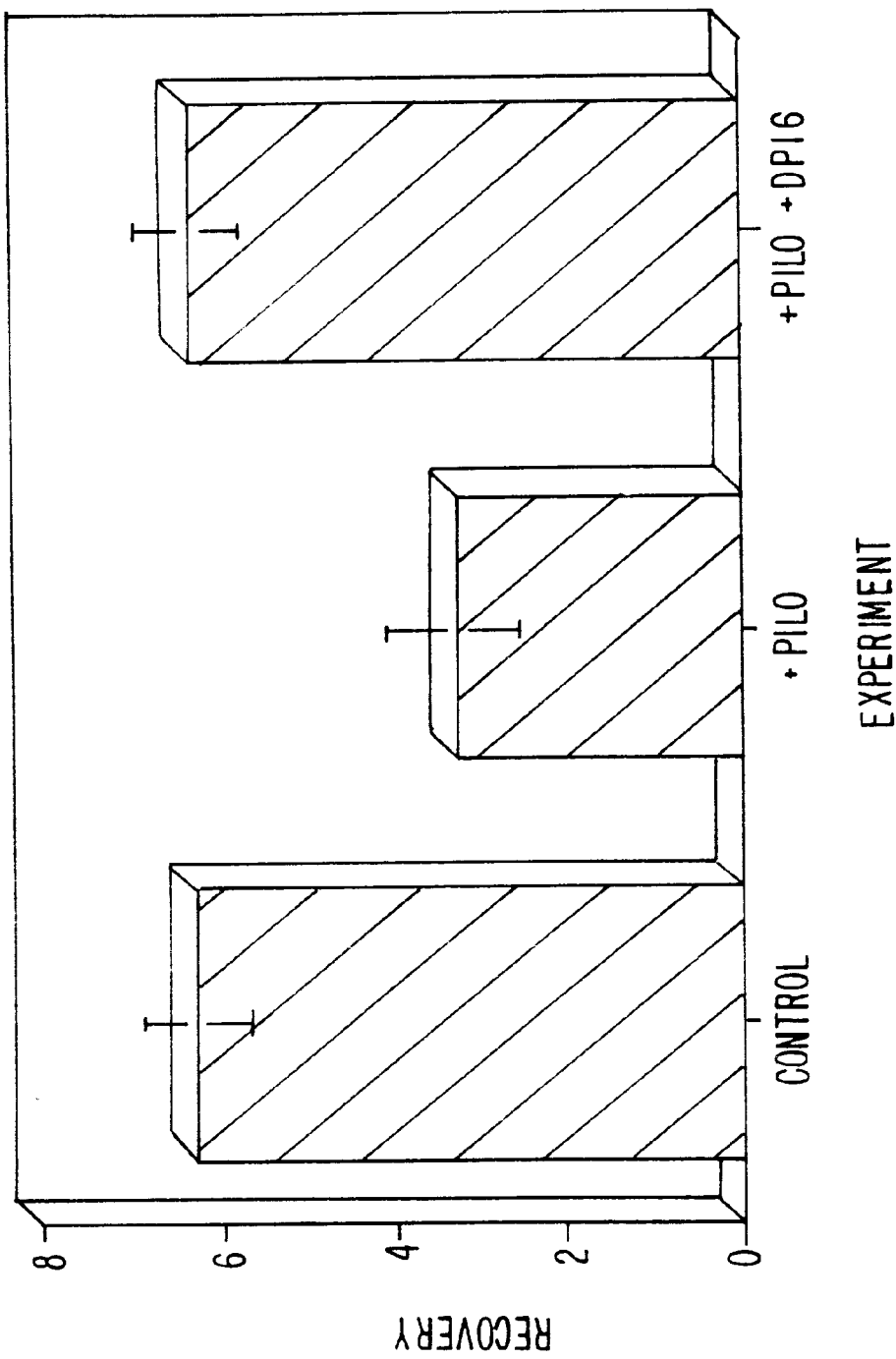
FIG. 7 illustrates the recovery of pilocarpine-damaged hearts in an Ischemia-Reperfusion model, when using a compound in accordance with an embodiment of the invention.

Langendorff's Heart Model. FIG. 6 shows Coronary Vessels Perfusion Resistance (CVPR) in isolated Langendorff's hearts. In the first 30 min of control isolated Langendorff's hearts CVPR steadily increased and this elevation is statistically significant after 20 min. In all hearts, perfused after pilocarpine administrations, initial perfusion flow was larger then in control, and subsequent CVPR significantly decreased (bottom line). This decrease of coronary vessels' tone possibly connected with intracardial noradrenaline deficiency or paralysis, evoked by hypoxia. Treatment of rats with DP 16 prior to pilocarpine application prevents damage of CVPR regulation in both the initial and final periods of perfusion, thus providing evidence relating to the ability of DP 16 to normalize coronary vessels function under hypoxic conditions. Cessation of perfusion for 30 min and subsequent reperfusion is characterized by the well-known broad class of cardiac damage events, which we classified with an arbitrary scale as shown in FIG. 7. Control hearts from non-treated rats mostly restored after stopping of perfusion with distinct range of alterations (as impaired myocardial excitability, conductivity and contractility). Mean point of recovery in control group is 6.3±0.6 (n=7). Hearts from pilocarpine-treated rats on different stages of PSCP demonstrated an increase of the spectrum and severity of pathological events, as the mean point of recovery was just 3.3±0.8. n=7, p<0.05. Recovery was frequently accompanied by ventricular fibrillation. Some of the hearts were not restored completely or restored atrial activity only. DP 16 treatment prior to pilocarpine administrations increased ability of damaged hearts to restore after reperfusion cessation: the mean point was 6.4±0.6 (n=9). In this group of rats we met more often with cases of complete recovery. Thus. DP16 treatment of pilocarpine-induced heart damage (PSCP) produced a definite improvement in cardiac function.

Investigation of Antiepileptic Effects of DP16: Metrazol Minimal Seizures Test

Method

Trial of DP16 as a possible antiepileptic drug was performed on 3–4 week old male BALB/c mice (18–27 g). Animals were maintained on an adequate diet and allowed free access to food and water except briefly during the experimental period. Animals were separately housed for one hour in transparent plastic cages before treatment and during the experimental period. Drugs were dissolved in normal saline with injection volume adjusted to 0.01 ml/g of body weight. DP16 was administered i.p., in doses ranging from 0.1 to 300 μg/kg: (0.1 μg/kg: n=10, 5 μg/kg: n=10, 25 μg/kg: n=20, 75 μg/kg: n=20, 150 μg/kg: n=20, and 300 μg/kg: n=10 animals respectively). Control animals received injections i.p. of normal saline. DP16 or saline administration followed in 30 minutes by Metrazol (50 μg/kg, s.c.). Subsequently epileptic signs were observed for the next 30 minutes. Absence or relative delay of myoclonic Jerks (MJ) in the experimental group was considered as indication of possible antiepileptic activity. Data were analyzed according to method c2 (chi-square) with the computer statistic package "StatViewII".

Results and Conclusions

Figure 8:
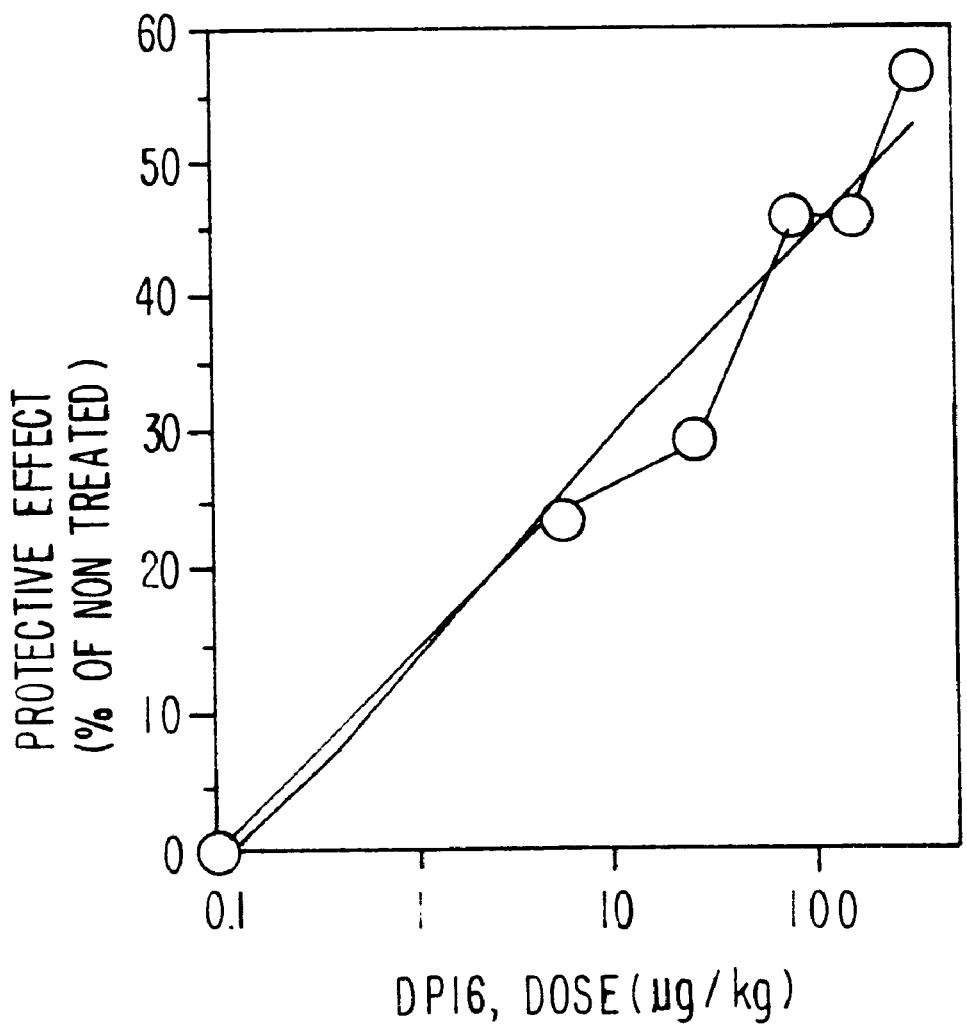
FIG. 8 illustrates the protective effect in a metrazol minimum seizures test, afforded by a compound in accordance with an embodiment of the invention.

Metrazol in a dosage of 50 μg/kg. s.c. caused myoclonic Jerks (MJ) in all of control mice with a latent period of 1011 min (n=11). The effect of DP16 on the appearance of minimal metrazol induced seizures is shown in FIG. 8. Mice treated with 0.1 μg/kg DP16 showed the same response to metrazol as control (untreated) animals. DP16 in doses ranging from 5 to 300 μg/kg exhibited a significant protective effect (p<0.001). The results of the test suggest a significant dose-dependent antiepileptic effect of DP16 on the metrazol induced seizures.

Investigation of Cardioprotective Effect of DP16

1. Trial on Ex Vivo Rat Heart Low-flow—Reperfusion Model

Method and Results

Broadly used ex vivo Langendorff's heart Stop-flow—Reperfusion and Low-flow models (Neely and Rovetto, 1975) remained conventional for pharmacological trials. Cardioprotective effect of DP16 was evaluated in a combined experimental paradigm of Normal flow perfusion followed by Low-flow and then by Reperfusion (LFR) of ex vivo rat heart. Evolution of ECG and of perfusion pressure (PP) was considered as a criterion for the drug evaluation. Data collected in experiments in the presence of DP16 were compared with one without drug supplement (control no. 1). An additional set of experiments (control no. 2) was performed with mixture of the components comprising DP16: BAPTA & lysophosphatidylcholine (LPC). DP16 (1–100 µg/L) was dissolved in a regular perfusion buffer. The mixture of BAPTA & LPC was dissolved in DMSO as a stock solution; the final concentration of BAPTA, LPC and DMSO in the perfusion buffer for control no. 2 was 100 µg/L of each component.

Figure 9A:
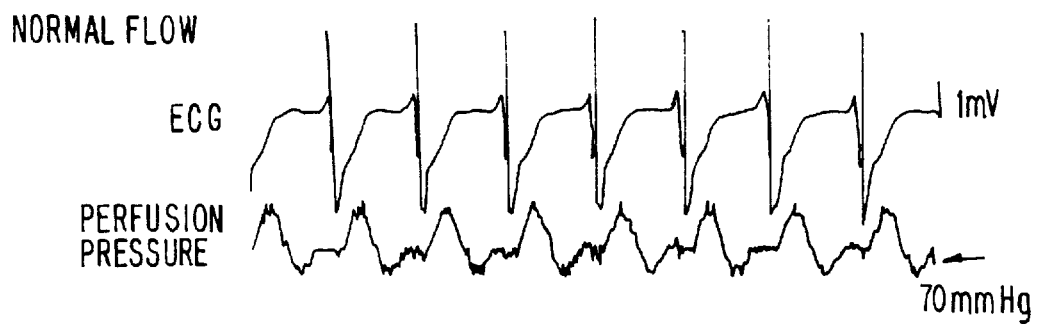
FIGS. 9A to C, 10A to D and 11A to D illustrate results of experiments in hypoxia-reperfusion cardiopathology.
Figure 9B:
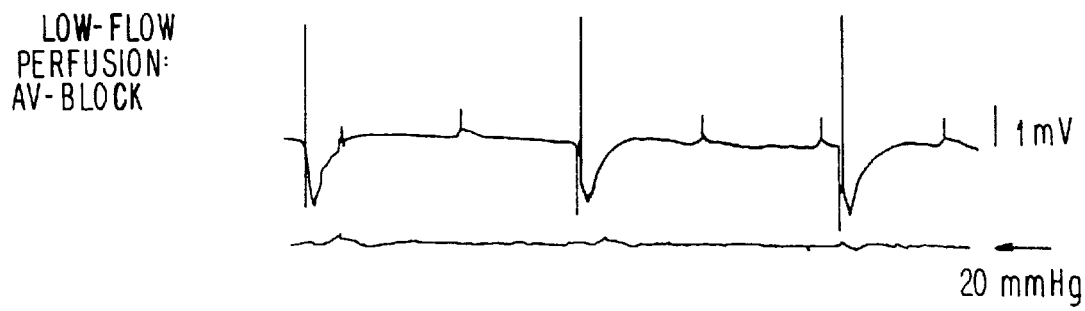
Figure 9C:
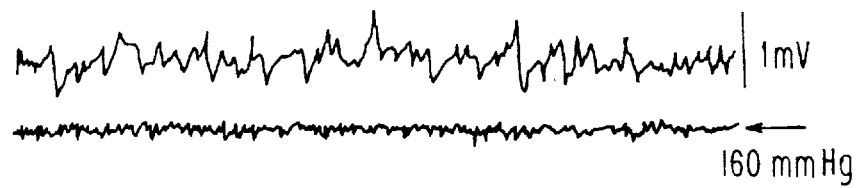
Figure 10A:
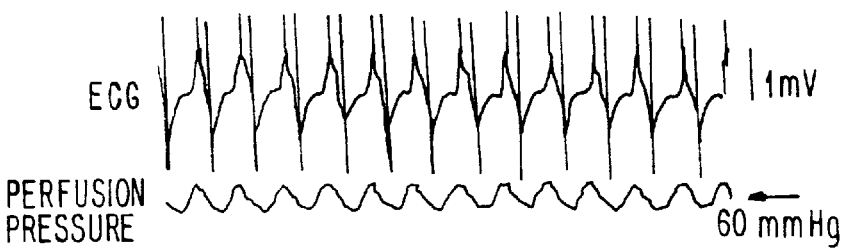
Figure 10B:
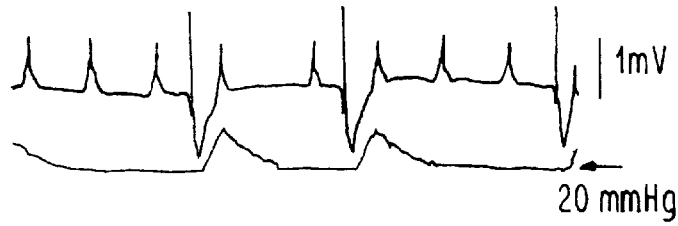
Figure 10C:
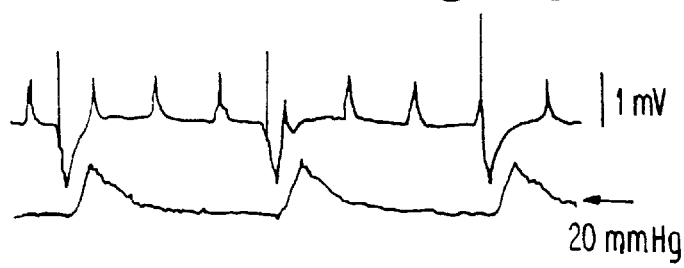
Figure 10D:
Figure 11A:
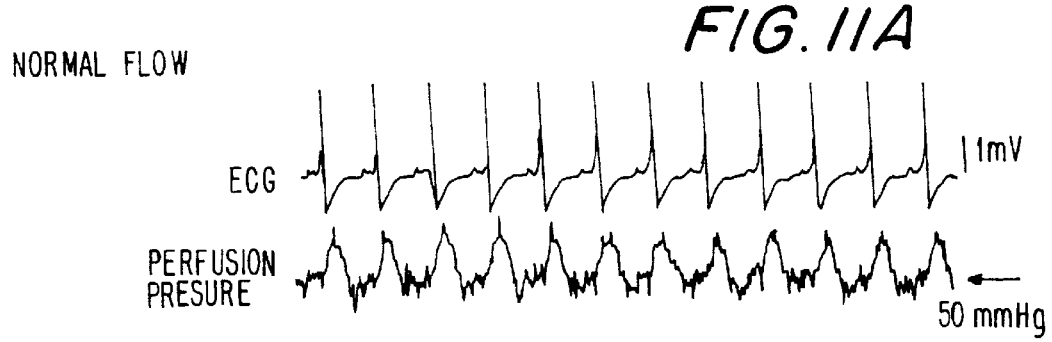
Figure 11B:
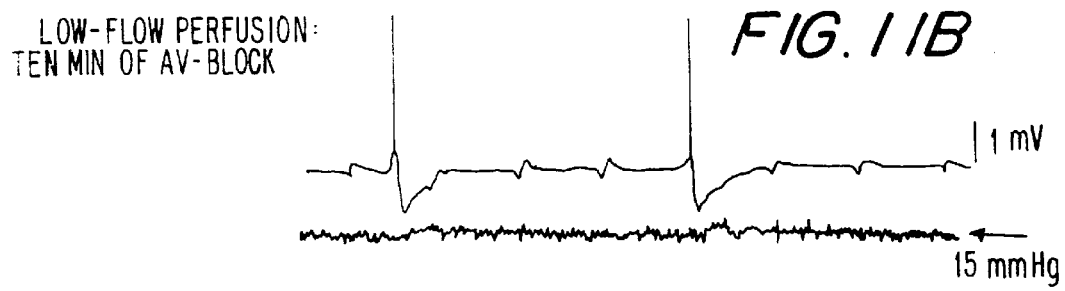
Figure 11C:
Figure 11D:
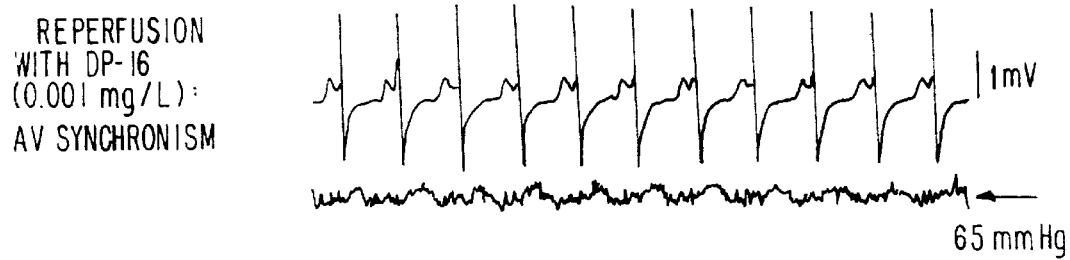

A severe decrease in perfusion pressure (PP) below 20 mm Hg (low-flow period) caused a sinus bradycardia culminated by stable AV block (FIG. 9B, c.f. normal flow in FIG. 9A) frequently with ventricular arrhythmia (9 experiments, control 1) Long term (>0.5 h) low-flow conditions usually ended by paroxysmal tachyarrhytlmia andventricular fibrillation (VF). Reperfusion started before VF could temporary restore sinus rhythm. However, reperfusion in most of the control experiments caused increase of coronary vascular tone and arrhythmia followed by irreversible VF (FIG. 9C). After establishment of AV block in low-flow period perfusion medium was supplemented by the drugs. No therapeutic effect on AVB was observed in the experiments with mixture of BAPTA & LPC (FIG. 10C and 10D, c.f. without BAPTA and LPC—normal flow in FIG. 10A and low flow perfusion in FIG. 10B). While addition of DP16 caused complete or temporal relief of atreoventricular synchronism (4 and 1 cases respectively) (FIG. 11C). Moreover, DP16 exhibited notable cardioprotective effect in the reperfusion period: full restoration of, the sinus rhythm was observed in 4 out of 5 experiments (FIG. 11D; c.f. without DP16 —normal flow in FIG. 11A and low flow perfusion in FIG. 11B). ECG analysis revealed mainly metabolic type of DP action: enhancing of atrial (definite increase of the heart rate) and ventricular (restoration of regular sinus rhythm) excitability. However, residual delay of AV conductivity (increased PQ interval) was observed.

Conclusions

The data obtained in this experiment suggest significant cardioprotective activity of DP16 in ischemia—reperfusion pathology.

Investigation of Cardioprotective Effect of DP16

2. Trial on In Vivo Model of Myocardial Damage
Method and Results

Administration of the potent β-adrenoreceptor agonist isoproterenol (ISO) is commonly accepted model of experimental myocardial pathology. The cardioprotective effect of DP16 was tested on 82 Sprague-Dawley female rats weighing 250–350 g. Myocardial damage was induced in rats by two consecutive injections of ISO (85 µg/kg, s.c.). When appropriate, the injections of ISO were followed in 30 and 180 minutes by DP16 (0.01 µg/kg. i.p.). The effect or DP16 was estimated by ECG analysis and determination or serum glutamic-oxaloacetat transaminase (SGOT) and lactotdehydrogenase (LDH) activity. Mortality of control rats after ISO intervention was 7.1±5.9% (7 out of 41). The surviving animals exhibited striking hyperacute deviation ST-segment in lead 1 and 2 ECG. Pathological signs on ECG were aggravated during the experimental period. In 48 hours after the second ISO injection all treated animals displayed pathological displacement of ST-segment. Administration of DP16 decreased mortality in 2 cases (2 out of 30). Animals receiving DP16 exhibited significantly (p<0.05) fewer alterations in the ECG. Pathological displacement of the ST-segment was found only on 28 and 40% of ECG (in 24 and in 48 hours following ISO respectively). Biochemical determination demonstrated a 1.7–1.9 fold increase if SGOT and LDH in ISO treated control rats (p<0.05). Treatment with DP16 substantially decreased the percentage of experimental animals exhibiting abnormal level of SGOT and LDH activity.

Conclusions

The data above suggest a significant cardioprotective effect of DP16 in an in vivo model of myocardial pathology.

General Conclusions

The prodrug denoted DP16 exhibited significant therapeutic and protective effects in experimental models of stroke & ischemia as well as in models of epilepsy, comparable with using the corresponding drug in conventional form in an amount which is $10^5$–$10^6$ times the amount when used in the form of the prodrug of the invention.

EXAMPLE 5

Preparation of Prodrug-3

"Prodrug-3" is the name used herein to denote a 1:1 ester of 1,2-bis-(2-aminophenoxy)ethane-N,N,N',N'-tetraacetic acid (BAPTA) with 1-myristylmyristyl alcohol and is prepared as follows. A solution of BAPTA (0.5 g, 1.05 mmol) in dimethylformamide (25 ml, freshly distilled over $CaH_2$), 1-myristylmyristyl alcohol (0.451 g, 1.1 mmol), N,N'-dicyclohexylcarbodiimide (0.216 g, 1.1 mmol) and 4-dimethylaminopyridine (0.025 g, 0.202 mmol) were stirred together for two days at room temperature under argon, in a 50 ml flask equipped with a magnetic stirrer. After two hours, N,N'-dicyclohexylurea began to precipitate. The reaction was monitored by TLC (90:10 v/v chloroform:methanol); $R_f$ of the product=0.62. The precipitate was removed by filtration and the filtrate was concentrated at 35° C. in vacuum. The residue was extracted with 25 ml of a 2:1:2 v/v mixture of chloroform:isopropanol:water. The organic layer was separated, washed with 1% aq. NaCl solution and dried over $Na_2SO_4$; it was then evaporated and the residue was passed through a 160×30 mm column of Kieselgel 60 (230–400 mesh ASTM), the desired product being eluted with a 90:10 v/v chloroform:methanol mixture. The 1-myristylmyristyl alcohol was prepared according to the method of Molotkovski, V. G. and Bergelson, L. D. (Biologicheska Chimia, 1982, 8(9): 1256–1262). The BAPTA-1-myristylmyristyl alcohol ester link in Prodrug-3 is susceptible to digestion by esterases.

EXAMPLE 4

Preparation and Biological Properties of TVA16

"TVA16" is the name used herein to denote a 1:1 ester of valproic acid with the choline derivative $ROCH_2$—CH(OH)—$CH_2O$—$OCH_2N^+(CH_3)_2$, where R is hexadecanoyl, and was prepared as follows. A solution of 1-hexadecanoyl-sn-glycero-3-phosphorylcholine (1.04 mmol) in chloroform (25 ml, freshly distilled over $P_2O_5$), valproic acid (0.159 g, 1.1 mmol), N,N'-dicyclohexylcarbodiimide (0.216 g, 1.1 mmol) and 4-dimethylaminopyridine (0.025 g, 0.202 mmol) were stirred together for two days at room temperature under argon, in a 50 ml flask equipped with a magnetic stirrer and glass beads (10 g, 5 mm diameter). After two hours, N,N'-dicyclohexylurea began to precipitate. The reaction was monitored by TLC (65:25:4 v/v chloroform:methanol:water); $R_f$ of the product=0.41. The precipitate and glass beads were removed by filtration and the filtrate was concentrated at 35° C. in vacuum. The residue was extracted with 25 ml of a 2:1:2 v/v mixture of chloroform:isopropanol:water. The organic layer was separated, washed with 1% aq. NaCl solution and dried over $Na_2SO_4$; it was then evaporated and the residue was passed through a 160×30 mm column of Kieselgol 60 (230–400 mesh ASTM), the desired product being eluted with a 65:25:4 v/v chloroform:methanol:water mixture; $R_f$=0.4.

A test sample of TVA16 was administered i.p. (0.01 to 100 mg/kg) to a group of three mice, one hour before an s.c. dose of metrazol (80 mg/kg). An effective dose was the amount which prevented convulsions (scored 2 points per animal) and/or death (scored 1 point per animal) in the subsequent 30 minutes. On this basis, the $ED_{100}$ could be calculated and is compared to known anticonvulsants in the following table.

| Anticonvulsant activity ($ED_{100}$, mg/kg) of known drugs and TVA16 | | | |
|---|---|---|---|
| chlordiazepoxide | 25 | muscimol (i.p.) | 2.5 |
| diazepam | 2.5 | nifedipine | >100 |
| diphenylhydantoin | >100 | nimodipine | >300 |
| flunarizine | >300 | phenobarbital | 50 |
| glutethimide | 150 | sodium valproate | 500 |
| meprobamate | 200 | verapamil | >100 |
| MK-801 | 0.5 | TVA16 | 0.6 |

From the above data it may be seen that TVA16 has significant anticonvulsant activity and appears to be more than 500× as potent as sodium valproate.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

I claim:

1. A method for treating a disease or disorder selected from the group consisting of localized tissue ischemia, stroke, epilepsy, asthma and allergy in a mammal comprising administering to a mammal having said disease or disorder, an amount of a pharmaceutically acceptable prodrug effective to treat the disease or disorder, said prodrug comprising a pharmacologically active carboxylic acid covalently bonded to an intracellular transporting adjuvant selected from the group consisting of hydroxy-$C_{2-6}$-alkyl esters of lysophosphatidic acids and lysophospho-lipids, said prodrug being cell membrane permeable and said covalent bond being cleaved in the presence of supranormal enzyme activity and
cleavage of said covalent bond results in selective intracellular activation of therapeutic amounts of the pharmacologically active carboxylic acid with cells having supranormal intracellular enzyme activity.

2. The method according to claim 1, wherein said pharmacologically active carboxylic acid is selected from the group consisting of branched-chain aliphatic carboxylic acids, salicylic acids, steroidal carboxylic acids, monoheterocyclic carboxylic acids and polyheterocyclic carboxylic acids.

3. The method according to claim 1, wherein said pharmacologically active compound is a calcium chelating agent.

4. The method according to claim 3, wherein said pharmacologically active compound comprises a carboxylic acid compound of the formula:

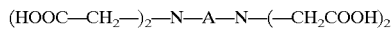

where A is a linking radical selected from the group consisting of an aliphatic, aromatic and heterocyclic organic radical comprising from 2–8 carbon atoms interrupted by 0, 2, 3, or 4 non-adjacent oxygen atoms, so that said carboxylic acid compound is an ester when there are 2, 3 or 4 non-adjacent oxygen atoms, and said carboxylic acid compound is covalently linked to a pharmaceutically acceptable alcohol containing from 3 to 32 carbon atoms and from 1–3 hydroxyl radicals; and pharmaceutically acceptable salt thereof; provided that, when said carboxylic acid compound is an ester, the nitrogens flanking A are not linked to any of said non-adjacent oxygen atoms.

5. The method according to claim 4, wherein said pharmaceutically acceptable alcohol is a $C_{7-32}$ secondary monohydric alcohol.

6. The method according to claim 4 wherein said pharmaceutically acceptable alcohol contains from 3 to 6 carbon atoms and from 1 to 3 hydroxyl radicals.

7. The method according to claim 4 wherein said linking radical A is selected from the group consisting of —(CH$_2$CH$_2$)$_m$—, where m is a number ranging from 1 to 4, and —CR=CR—O—CH$_2$CH$_2$—O—CR'=CR'—, wherein each pair of radicals R—R and R'—R', together with the attached —C=C—moiety, complete an aromatic or heterocyclic ring containing from 5 to 6 ring atoms, the ring completed by R—R being the same as or different from the ring completed by R'—R'; wherein 0, 2, 3 or 4 carbon atoms of—(CH$_2$CH$_2$)$_m$— are each replaced by oxygen.

8. The method according to claim 4 wherein said linking radical A is selected from the group consisting of —CH$_2$CH$_2$— and —CH$_2$CH$_2$—O—CH$_2$CH$_2$—O—CH$_2$CH$_2$—.

9. The method according to claim 4 wherein said linking radical A is —CR=CR—O—CH$_2$CH$_2$—O—CR'=CR'—, where each of the pairs of radicals R—R and R'—R', together with the attached —C=C—moiety, complete an aromatic or heterocyclic ring which is selected from the group consisting of furan, thiophene, pyrrole, pyrazole, imidazole, 1,2,3-triazole, oxazole, isoxazole, 1,2,3-oxadiazole, 1,2,5-oxadiazole, thiazole, isothiazole, 1,2,3-thiadiazole, 1,2,5-thiadiazole, benzene, pyridine, pyridazine, pyrimidine, pyrazine, 1,2,3-triazine, 1,2,4-triazine, and 1,2-, 1,3- and 1,4-oxazines and -thiazines, the ring completed by R—R being the same as or different from the ring completed by R'—R'.

10. The method according to claim 9, wherein said linking radical A is —CR=CR—O—CH$_2$CH$_2$—O—CR'=CR'—, where each of the pairs of radicals R—R and R'—R', together with the attached —C=C— moiety, completes the same or different rings selected from unsubstituted and substituted benzene rings, in which substituted benzene rings contain from 1–4 substituents selected from the group consisting of $C_{1-3}$-alkyl, $C_{1-3}$-alkoxy, fluorine, chlorine, bromine, iodine and $CF_3$, or a single divalent substituent which is —O—(CH$_2$)$_n$—O— and n is a number from 1 to 3.

11. The method according to claim 3 wherein said chelating agent is selected from the group consisting of ethylene-1,2-diamine-N,N,N',N'-tetraacetic acid, ethylene-1,2-diol-bis-(2-aminoethyl ether)-N,N,N',N'-tetraacetic acid and 1,2-bis-(2-aminophenoxy)ethane-N,N,N',N'-tetraacetic acid.

12. The method according to claim 4 wherein said pharmaceutically acceptable alcohol contains from 3 to 6 carbon atoms and from 1 to 3 hydroxyl radicals.

13. The method according to claim 4, wherein said pharmaceutically acceptable alcohol comprises at least one member of the group consisting of hydroxy-$C_{2-6}$-alkyl esters of lysophosphatidic acids and lysophospholipids.

14. The method according to claim 4, wherein said ester is a chelating agent selected from the group consisting of ethylene-1,2-diamine-N,N,N',N'-tetraacetic acid, ethylene-1,2-diol-bis-(2-aminoethyl ether)-N,N,N',N'-tetraacetic acid and 1,2-bis-(2-aminophenoxy)ethane-N,N,N',N'- tetraacetic acid.

15. The method according to claim 1, wherein the prodrug is administered by a route selected from the group consisting of intramuscular injection, intravenous injection, infusion into a body cavity, cerebrospinal injection, localized infiltration of a target tissue, buccal absorption and aerosol inhalation in an amount effective to treat said disease or disorder.

16. The method according to claim 1, wherein said intracellular transporting adjuvant comprises at least one pharmaceutically acceptable alcohol which is selected from the group consisting of lyso-plasmalogens, lysophosphatidic acid amides, and lysophosphatidyl-ethanolamine.

17. The method according to claim 4, wherein said pharmaceutically acceptable alcohol comprises at least one member of the group consisting of lyso-plasmalogens, lyso-phosphatidic acid amides, and lysophosphatidyl-ethanolamine.

* * * * *